(12) United States Patent
Rossignol et al.

(10) Patent No.: US 7,348,316 B2
(45) Date of Patent: Mar. 25, 2008

(54) USE OF AN ANTI-ENDOTOXIN DRUG IN THE PREVENTION AND TREATMENT OF DISEASE

(75) Inventors: Daniel P. Rossignol, Mahwah, NJ (US); Melvyn Lynn, East Brunswick, NJ (US); Clifford DiLea, Spring Lake, NJ (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/010,516

(22) Filed: Dec. 13, 2004

(65) Prior Publication Data

US 2005/0153929 A1 Jul. 14, 2005

Related U.S. Application Data

(63) Continuation of application No. PCT/US03/19022, filed on Jun. 13, 2003.

(51) Int. Cl.
*A61K 31/70* (2006.01)
(52) U.S. Cl. ..................................... 514/53
(58) Field of Classification Search .................. 514/53
See application file for complete search history.

(56) References Cited

U.S. PATENT DOCUMENTS

| 4,997,430 A | 3/1991 | Van der Heiden et al. |
| 5,681,824 A | 10/1997 | Christ et al. |
| 5,756,718 A | 5/1998 | Kobayashi et al. |
| 5,935,938 A | 8/1999 | Christ et al. |

FOREIGN PATENT DOCUMENTS

| EP | 0 536 969 A | 4/1993 |
| WO | WO 00/41703 | 7/2000 |
| WO | WO 01/37843 A | 5/2001 |

OTHER PUBLICATIONS

Cooke et al., "LPS Antagonism Reduces Graft-Versus-Host Disease and Preserves Graft-Versus-Leukemia Activity After Experimental Bone Marrow Transplantation," The Journal of Clinical Investigation 107(12):1581-1589, 2001.
Hawkins et al., "A Novel Class of Endotoxin Receptor Agonists with Simplified Structure, Toll-Like Receptor 4-Dependent Immunostimulatory Action, and Adjuvant Activity," The Journal of Pharmacology and Experimental Therapeutics 300(2): 655-661, 2002.
Kawata et al., "E5531, a Synthetic Non-Toxic Lipid A Derivative Blocks the Immunobiological Activities of Lipopolysaccharide," British Journal of Pharmacology 127:853-862, 1999.
Kobayashi et al., "Suppression of Murine Endotoxin Response by E5531, a Novel Synthetic Lipid A Antagonist," Antimicrobial Agents and Chemotherapy 42(11):2824-2829, 1998.
Lynn et al., "Extended in Vivo Pharmacodynamic Activity of E5564 in Normal Volunteers with Experimental Endotoxemia," The Journal of Pharmacology and Experimental Therapeutics 308(1):175-181, 2004.
Rose et al., "Consequences of Interaction of a Lipophilic Endotoxin Antagonist with Plasma Lipoproteins," Antimicrobial Agents and Chemotherapy 44(3):504-510, 2000.
Rossignol et al., "Safety, Pharmacokinetics, Pharmacodynamics, and Plasma Lipoprotein Distribution of Eritoran (E5564) during Continuous Intravenous Infusion into Healthy Volunteers," Antimicrobial Agents and Chemotherapy 48(9):3233-3240, 2004.
Wasan et al., "Lipoprotein Distribution of a Novel Endotoxin Antagonist, E5531, in Plasma from Human Subjects with Various Lipid Levels," Antimicrobial Agents and Chemotherapy 43(10):2562-2564, 1999.

*Primary Examiner*—Elli Peselev
(74) *Attorney, Agent, or Firm*—Clark & Elbing LLP

(57) ABSTRACT

The invention provides methods for preventing and treating disease involving the use of an anti-endotoxin drug.

7 Claims, No Drawings

USE OF AN ANTI-ENDOTOXIN DRUG IN THE PREVENTION AND TREATMENT OF DISEASE

CROSS-REFERENCE TO RELATED APPLICATIONS

This application is a continuation of PCT/US03/19022, filed Jun. 13, 2003, which claims priority from U.S. Ser. No. 10/171,478, filed Jun. 13, 2002 (now abandoned), which is a continuation-in-part of U.S. Ser. No. 09/879,718, filed Jun. 11, 2001 (now abandoned), which claims priority from U.S. Ser. No. 60/210,638, filed Jun. 9, 2000 (now abandoned). The contents of each of these applications are incorporated herein by reference.

BACKGROUND OF THE INVENTION

This invention relates to a regimen of administration of an anti-endotoxin drug, as well as methods for the prevention or treatment of graft-versus-host disease.

Since the 1930's, the increasing use of immunosuppressive therapy and invasive devices, as well as the increased incidence of antibiotic resistance in bacteria, have led to a gradual rise in the occurrence of sepsis and septic shock. Currently, the estimated incidences in the U.S. of sepsis and septic shock are greater than 400,000 and greater than 200,000 patients/year, respectively. This results in about 100,000 fatalities/year, making septic shock the most common non-coronary cause of death in the hospital Intensive Care Unit (ICU). Currently, ICU therapy for septic shock is limited to antibiotic therapy, cardiovascular resuscitation, Vasopressor/ionotrope therapy, and ventilatory support. This ICU care can cost up to $1,500/day and average a total of $13,000 to $30,000 per patient.

It is likely that antibiotics themselves can worsen morbidity associated with sepsis; their bactericidal action can result in the release of endotoxin from Gram negative bacteria, which are believed to induce many pathophysiological events such as fever, shock, disseminated intravascular coagulation (DIC), and hypotension. Further, endotoxin can be detected in the blood of patients regardless of pathogen. Consequently, medicines for the treatment of gram-negative sepsis have been desired for some time, especially drugs capable of blocking endotoxin or cytokines derived from endotoxin-mediated cellular stimulation. To this end, various strategies for treatment have included use of antibodies against LPS or cytokines, such as tumor necrosis factor-α (TNF-α) and interleukin-1. For various reasons, these approaches have failed.

While endotoxin itself is a highly heterogenous molecule, the expression of many of the toxic properties of endotoxin is attributed to a highly conserved hydrophobic lipid A portion. An effective drug that acts as an antagonist to this conserved structure is known as E5564 (also known as compound 1287 and SGEA). This drug is described as compound 1 in U.S. Pat. No. 5,681,824, which is incorporated herein by reference. E5564 has the formula:

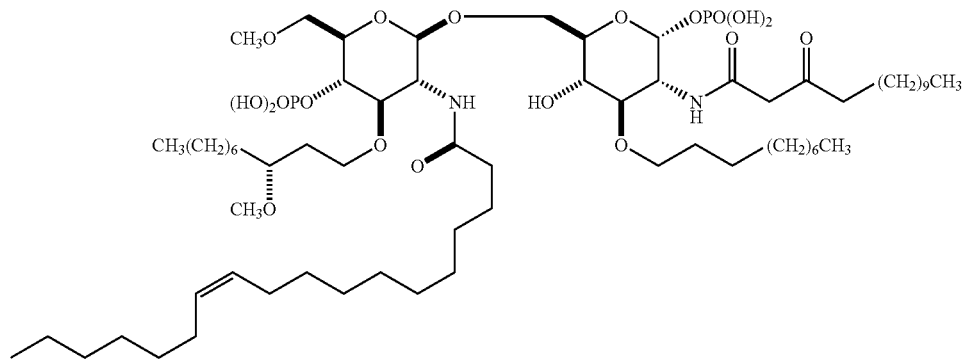

(α-D-Glucopyranose, 3-O-decyl-2-deoxy-6-O-[2-deoxy-3-O-[(3R)-3-methoxydecyl)-6-O-methyl-2-[[(11Z)-1-oxo-11-octadecenyl)amino]-4-O-phosphono-β-D-glucopyranosyl]-2-[(1,3-dioxotetradecyl)amino]-,1-(dihydrogen phosphate), which can be provided as a tetrasodium salt. E5564 has a molecular weight of 1401.6.

SUMMARY OF THE INVENTION

We have discovered that administration of E5564 by loading dose followed by maintenance dosing, or by single bolus injection, is effective in the prevention or treatment of the clinical effects of endotoxemia.

Accordingly, the invention features a method of treating a patient, such as a human patient, that has or is at risk of developing a medical condition that is amenable to treatment with Compound E5564. In this method, Compound E5564 is administered to the patient by bolus or intermittent intravenous infusion. The bolus infusion can be of 0.4-60 mg, e.g., 6-56 mg or 2-28 mg drug, over the course of, e.g., 4 hours. The administration can be by intermittent infusion, in which a loading dose (of, e.g., 0.4-60 mg, 6-56 mg, or 12-28 mg drug, over a period of, e.g., 4 hours) is administered, followed by a maintenance dose. Optionally, a second loading dose (of, e.g., 0.4-60 mg, 6-56 mg, or 12-28 mg drug, over a period of, e.g., 2 hours) can be administered at about 12 or about 24 hours after the first loading dose. The maintenance dose can be administered over a period of, e.g., 2 hours, about 12 hours after the previous loading dose. Also, an additional maintenance dose, or additional maintenance doses, can be administered, that are each administered over a period of 2 hours, about 12 hours from the previous maintenance dose.

In a specific example of a method of the invention, a first loading dose of 3 mg/hour is administered for four hours, followed by a second loading dose of 3 mg/hour for two hours at 12 hours after the first loading dose, followed by a maintenance dose of 1.5 mg/hour for two hours at 12, 24, 36, 48, 60, 72, 84, 96, and 108 hours after the second loading dose.

Patients that can be treated according to the methods of the invention include, for example, surgical patients (e.g., cardiac surgical patients), patients that have or are at risk of developing endotoxemia, sepsis, or septic shock, patients that are infected with HIV, and patients that are suffering from an immunological disorder, such as allograft rejection or graft-versus-host disease. The methods of the invention can also be carried out with any patients that have had, will have, or are having any type of transplant. For example, the methods can be carried out with patients having leukemia (e.g., chronic myeloid leukemia, acute myeloid leukemia, or acute lymphocytic leukemia) or another cancer, and that are treated by bone marrow or stem cell transplantation. The patients can also be kidney, liver, heart, or lung transplant patients. The graft-versus-host disease that is prevented or treated, according to the invention, can be acute or chronic.

The methods of the invention provide significant therapeutic benefits and are easily carried out, especially with many of the patients treated according to the methods of the invention, who already have intravenous lines inserted, as part of their treatment in the ICU. Further, the methods of the invention provide an approach to preventing and treating graft-versus-host disease.

Other features and advantages of the invention will be apparent from the following detailed description and the claims.

DETAILED DESCRIPTION

We have discovered that administration of E5564 to humans in a single bolus or by intermittent infusion is effective at preventing the clinical effects of endotoxemia. Our previous studies have shown that the activity of the drug decreases rapidly upon cessation of administration, although it is not cleared from circulation, indicating the desirability of continuous infusion. We have now discovered that administration of doses of the drug that are higher than the minimum dose found to be effective in endotoxin challenge studies results in prolonged activity of the drug, after cessation of administration. Thus, we have discovered drug administration regimens involving single bolus or intermittent infusion, to prevent or treat endotoxemia and related conditions and disorders (e.g., sepsis) in humans.

According to the invention, the drug can be administered in a single bolus by intravenous infusion through, for example, a central access line or a peripheral venous line, or by direct injection, using a syringe. Such administration may be desirable if a patient is only at short-term risk for exposure to endotoxin, and thus does not need prolonged persistence of the drug. For example, this mode of administration may be desirable in surgical patients, such as patients having cardiac surgery, e.g., coronary artery bypass graft surgery or valve replacement surgery. In these patients, a single bolus infusion of, e.g., 0.10-15 mg/hour (e.g., 0.5-7 mg/hour, or 3 mg/hour) can be administered over a period of four hours prior to and/or during surgery. (Note that the amount of drug administered is based on an assumed average weight of a patient of 70 kg.) Shorter or longer time periods of administration can be used, as determined to be appropriate by one of skill in this art, provided that the absolute amount of drug administered, as indicated above, is maintained.

In cases in which longer term persistence of active drug is desirable, for example, in the treatment of a condition associated with long-term exposure to endotoxin, such as during infection, sepsis, when a patient is immunocompromised, when the gastrointestinal tract is damaged due to chemotherapy, radiation, or immunological activation, or in surgical situations in which it is determined that prolonged treatment is desirable, intermittent administration can be carried out. In these methods, a loading dose is administered, followed by either (i) a second loading dose and a maintenance dose (or doses), or (ii) a maintenance dose or doses, without a second loading dose, as determined to be appropriate by those of skill in this art.

The first (or only) loading dose can be administered in a manner similar to that described for the single bolus infusion described above. That is, 0.10-15 mg/hour (e.g., 0.5-7 mg/hour or 3 mg/hour) can be administered to a patient over a period of four hours prior to surgery. (As is noted above, and is applicable throughout this description, the time periods of administration can be varied, provided that plasma dosage levels are maintained.) If a second loading dosage is to be used, it can be administered about 12 hours after the initial loading dose, and can involve infusion of, e.g., 0.10-15 mg/hour (e.g., 0.5-7 mg/hour or 3 mg/hour) of drug over a period of, e.g., about two hours.

To extend the activity of the drug, a maintenance dose (or doses) of drug can be administered, so that levels of active drug are maintained in the blood of a patient. Maintenance doses can be administered at levels that are less than the loading dose(s), for example, at a level that is about ⅙ of the loading dose. Specific amounts to be administered in maintenance doses can be determined by a medical professional, with the goal that drug level is at least maintained. Maintenance doses can be administered, for example, for about 2 hours every 12 hours beginning at hour 24 and continuing at, for example, hours 36, 48, 60, 72, 84, 96, 108, and 120. Of course, maintenance doses can be stopped at any point during this time frame, as determined to be appropriate by a medical professional.

Specific examples of dosing regimens that are included in the invention are shown in the following table.

TABLE 1 dose levels and rates of E5564 administration to provide protection for 6 days

| | Loading Doses | | | Maintenance Dose[3] | | Total Dose |
|---|---|---|---|---|---|---|
| Dose level | Loading dose #1 (mg/hour) for 4 hours[1] | Loading dose #2 (mg/hr) for 2 hours[2] | Dose (mg) | Rate (mg/hour) for 2 hours | Dose (mg) | (mg) |
| I | 1 | 1 | 6 | 0.5 | 1 | 15 |
| II | 3 | 3 | 18 | 1.5 | 3 | 45 |
| III | 7 | 7 | 42 | 3.5 | 7 | 105 |

[1]Loading dose #1 given over 4 hours at beginning of treatment only.
[2]Loading dose #2 given over 2 hours at 12 hours only.
[3]Maintenance doses given over 2 hours every 12 hours at hours 24, 36, 48, 60, 72, 84, 96, 108, and 120, for a total of 9 maintenance doses.

The methods of the invention can be used in conjunction with any type of surgery or medical procedure that could lead to the occurrence of endotoxemia or related complications (e.g., sepsis syndrome). For example, the methods of the invention can be used in conjunction with cardiac surgery (e.g., coronary artery bypass graft, cardiopulmonary bypass, or valve replacement), transplantation (of, e.g., liver, heart, kidney, lung, or bone marrow), cancer surgery (e.g., resection of a tumor), or any abdominal surgery. Additional examples of surgical procedures with which the methods of the invention can be used include surgery for treating acute pancreatitis, inflammatory bowel disease, placement of a transjugular intrahepatic portosystemic stent shunt, hepatic resection, burn wound revision, and burn wound escharectomy. The methods of the invention can also be used in conjunction with non-surgical procedures in which the gastrointestinal tract is compromised. For example, the methods of the invention can be used in association with chemotherapy or radiation therapy in the treatment of cancer.

The methods of the invention can also be used in the treatment of conditions associated with human immunodeficiency virus (HIV) infection, and immunological disorders, such as allograft rejection and graft-versus-host disease (GVHD), in particular, acute GVHD. GVHD is the most common complication of patients who have undergone allogeneic bone marrow or stem cell transplantation. These patients include, for example, patients that have chronic myeloid leukemia (CML), acute myeloid leukemia (AML), or acute lymphocytic leukemia (ALL). In GVHD, immune cells (T lymphocytes) from the donor attack cells of the transplant recipient, which the donor immune cells recognize as being foreign. Any types of cells in the recipient can be recognized as being foreign, and thus attacked, by the donor T lymphocytes. These cells include cancer cells, in which case the effect, referred to as graft-versus-leukemia (GVL) effect, is beneficial to the recipient. The recognized and attacked cells can also include normal cells of, e.g., the skin, stomach, intestines, liver, and mucosal surfaces, and this recognition can lead to very severe or even lethal damage. Acute GVHD occurs shortly after transplantation and is caused by T lymphocytes present in the donor preparation, while chronic GVHD occurs 2-3 months after the transplant, and may be caused by T lymphocytes that have grown in an adverse manner from the graft.

The primary route by which donor T lymphocytes cause GVHD is by priming inflammatory cells (monocytes and macrophages) to secrete cytopathic amounts of cytokines when stimulated by bacterial lipopolysaccharide (LPS). The cytokines in turn directly damage tissues and organs, as well as provoke T cell expansion and increases in cytotoxic T lymphocytes (CTL) and natural killer (NK) cells, responses that can also damage tissues and organs. Thus, according to the present invention, patients that have or are at risk of developing acute or chronic GVHD (e.g., patients with CML, AML, or ALL that are treated by bone marrow or stem cell transplant) can be treated by the administration of an LPS antagonist, which blocks such stimulation. The LPS antagonist can be administered just before, during, and/or shortly after (e.g., during the first 4-21 days after) transplantation to prevent GVHD. GVHD has been detected with other types of transplantations as well, for example, with kidney, liver, heart, and lung transplants. The methods of the invention can be used in the prevention and treatment of GVHD occurring with these types of transplantations as well.

In the case of preventing or treating GVHD, antiendotoxin compounds can be administered using the doses and regimens described herein, or by use of other approaches determined to be appropriate by those of skill in the art.

The drug can be formulated according to standard pharmaceutical practice. A specific example of a formulation of the drug is described in detail in U.S. Ser. No. 60/452,022, the contents of which are incorporated herein by reference.

Compound E5564 is described in U.S. Pat. No. 5,935,938, which is incorporated herein by reference. The drug can be formulated, for example, by dissolving 35.4 mg of drug substance in 52.1 ml 0.01N NaOH, stirring for one hour at room temperature, and diluting into phosphate-buffered lactose. After adjusting the pH to 7.3 and diluting to a final concentration of 0.1 mg/ml E5564, the solution can be filter-sterilized and lyophilized. An example of a formulation of drug product in 1 ml vials is shown below.

TABLE 2

| Material | amount |
|---|---|
| E5564 | 100 µg |
| $NaH_2PO_4 \cdot 4H_2O$ | 0.35 mg |
| NaOH | 0.06 mg |
| Lactose hydrous | 100 mg |
| $Na_2HPO_4 \cdot 7H_2O$ | 0.45 mg |
| sterile water | 1 ml |

As is noted above, the drug is administered by infusion, either through a central access line or a peripheral venous line, or by direct infusion by use of a syringe.

All references cited herein are incorporated by reference in their entirety. Other embodiments are within the following claims.

What is claimed is:

1. A method of treating a human patient with a compound of the structure:

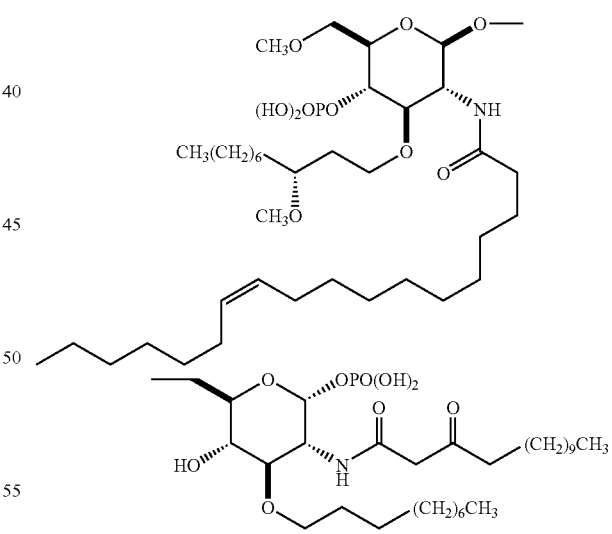

or a pharmaceutically acceptable salt thereof, wherein said patient has or is at risk of developing endotoxemia, sepsis, or septic shock, said method comprising administering said compound to said patient by intermittent intravenous infusion, comprising administration of a first loading dose, a second loading dose at about 12 or 24 hours after the first loading dose, followed by a maintenance dose.

2. The method of claim 1, wherein said first loading dose is 0.4-60 mg, 6-56 mg, or 12-28 mg drug.

3. The method of claim 1, wherein said first loading dose is administered over a period of 4 hours.

4. The method of claim 1, wherein the second loading dose is 0.4-60 mg, 6-56 mg, or 12-28 mg drug, administered over a period of 2 hours.

5. The method of claim 1, wherein the maintenance dose is administered over a period of 2 hours, about 12 hours after the previous loading dose.

6. The method of claim 5, further comprising administration of an additional maintenance dose or additional maintenance doses, that are each administered over a period of 2 hours, about 12 hours from the previous maintenance dose.

7. The method of claim 1, wherein a first loading dose of 3 mg/hour is administered for 4 hours, followed by a second loading dose of 3 mg/hour for 2 hours at about 12 hours after the first loading dose, followed by a maintenance dose of 1.5 mg/hour for 2 hours at about 12, 24, 36, 48, 60, 72, 84, 96, and 108 hours after the second loading dose.

\* \* \* \* \*